(12) United States Patent
Christoph et al.

(10) Patent No.: US 6,359,183 B1
(45) Date of Patent: *Mar. 19, 2002

(54) TREATMENT OF CHROMIUM OXIDE AND CATALYTIC MANUFACTURE OF VINYL FLUORIDE

(75) Inventors: Frank J. Christoph, Elkton, MD (US); George W. Coulston; Velliyur Nott Mallikarjuna Rao, both of Wilmington, DE (US)

(73) Assignee: E. I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/452,237

(22) Filed: Dec. 1, 1999

Related U.S. Application Data

(62) Division of application No. 08/973,379, filed as application No. PCT/US96/09752 on Jun. 7, 1996, now Pat. No. 6,034,289.
(60) Provisional application No. 60/004,058, filed on Sep. 20, 1995, and provisional application No. 60/000,066, filed on Jun. 8, 1995.

(51) Int. Cl.[7] ............................................. C07C 17/25
(52) U.S. Cl. ...................................... 570/156; 570/157
(58) Field of Search ................................. 570/156, 157

(56) References Cited

U.S. PATENT DOCUMENTS

| | | |
|---|---|---|
| 2,442,993 A | 6/1948 | Cass |
| 2,461,523 A | 2/1949 | Coffman et al. |
| 2,599,631 A | 6/1952 | Harmon |
| 2,892,000 A | 6/1959 | Skiles |
| 3,258,500 A | 6/1966 | Swamer |
| 3,413,363 A | 11/1968 | Pindzola |
| 4,843,181 A | 6/1989 | Gumprecht et al. |
| 5,036,036 A | 7/1991 | Lerou |
| 5,446,216 A | 8/1995 | Rao |
| 6,034,289 A | * 3/2000 | Christoph et al. ......... 570/156 |

FOREIGN PATENT DOCUMENTS

| | | |
|---|---|---|
| EP | 0 234 002 | 9/1987 |
| EP | 0 238 713 | 9/1987 |
| EP | 0 313 061 | 4/1989 |
| EP | 0 403 108 | 12/1990 |
| EP | 0 461 297 A1 | 12/1991 |
| GB | 921 254 | 3/1963 |
| GB | 2 012 739 | 8/1979 |

OTHER PUBLICATIONS

Ullman's Encyclopaedia of Industrial Chemistry, 5th Edition, vol. A7, p. 76, (1986).
Encyclopaedia of Chemical Technology, Kirk–Othmer, 4th Edition, vol. 6, p. 271 (1993).

* cited by examiner

*Primary Examiner*—Alan Siegel

(57) ABSTRACT

Advantageous processes are disclosed for the production of vinyl fluoride. Also disclosed are advantageous methods which may be employed for the preparation of catalysts useful in such processes. Included are methods which involve (i) reducing surface $B_2O_3$ present in a bulk chromium oxide composition containing surface $B_2O_3$ by treating said composition with HF at an elevated temperature and/or (ii) treating a bulk chromium oxide composition containing $B_2O_3$ to enrich the $B_2O_3$ present on its surface by heating said composition in oxygen or an oxygen-containing environment (e.g., air) at an elevated temperature for a time sufficient to enrich the $B_2O_3$ on the surface of the composition by at least a factor of two compared to the surface analysis of the untreated bulk composition. Processes are provided herein which involve contacting 1,1-difluoroethane in the vapor phase with a trivalent chromium catalyst (preferably a trivalent chromium catalyst having primarily the morphology of alpha-chromium oxide and/or containing less than 1000 ppm alkali metal as the alkali metal oxide) wherein chromium is at least 95 atom percent of the metallic cations of said catalyst, at a temperature between about 225° C. and 375° C. Advantageous embodiments of these processes are disclosed wherein (i) the catalyst is prepared by reducing $B_2O_3$ present in a bulk chromium oxide composition as indicated above, (ii) chromium is at least 99 atom percent of the metallic cations of the catalyst and/or (iii) the space velocity is from about 2000 volumes of 1,1-difluoroethane per volume of catalyst per hour.

2 Claims, No Drawings

TREATMENT OF CHROMIUM OXIDE AND CATALYTIC MANUFACTURE OF VINYL FLUORIDE

This application is a division of U.S. Pat application Ser. No. 08/973,379 filed Dec. 3, 1997, now U.S. Pat. No. 6,034,289 which represents the national filing under 35 USC 371 of International Application No. PCT/US96/09752 filed Jun. 7, 1996 and claims benefit of Provisional Application Ser. No. 60/000,066, filed Jun. 8, 1995 and Provisional Application Ser. No. 60/004,058, filed Sep. 20, 1995.

FIELD OF THE INVENTION

This invention relates to processes for the production of vinyl fluoride, and more particularly, to catalysts and catalytic processes for the dehydrofluorination of 1,1-difluoroethane to vinyl fluoride.

BACKGROUND

Vinyl fluoride (i.e., $CH_2=CHF$ or VF) is a useful monomer for the preparation of fluorocarbon polymers which have excellent weathering and chemical resistance properties.

Vinyl fluoride can be produced from acetylene and hydrogen fluoride using mercury catalysts. It can also be produced by the dehydrofluorination of 1,1-difuloroethane (i.e., $CHF_2CH_3$ or HFC-152a). U. S. Pat. No.2,892,000 discloses a process for the manufacture of vinyl fluoride and 1,1-difluoroethane. In this process HF and acetylene are passed over a chromium catalyst (e.g., a chromium oxide or chromium salt catalyst) to obtain mixtures of VF and HFC-152a. A process is also disclosed in this patent for the conversion of product HFC-152a to VF using these catalysts. The patent describes using for this conversion of HFC-152a, catalysts which have been used for the reaction of HF and acetylene and whose activity has been reduced; and have then been treated by passing air or oxygen over the heated catalyst (e.g., at about 600 to 700° C. for 1 to 3 hours) whereby it is activated for use in the dehydrofluorination of the HFC-152a to VF (e.g., at temperatures of from about 200° C. to 400° C. at a rate of about 20 to about 80 volumes per volume of catalyst per hour). There is an ongoing interest in developing more efficient catalysts for the conversion of HFC-152a to VF.

SUMMARY OF THE INVENTION

This invention provides advantageous processes for the production of vinyl fluoride and advantageous methods which may be employed for the preparation of catalysts useful in such processes. A method is provided to reduce surface $B_2O_3$ present in a bulk chromium oxide composition containing surface $B_2O_3$. The method comprises contacting said bulk chromium oxide composition with HF at an elevated temperature (e.g., from 200 to 400° C.). Also provided is a method for treating a bulk chromium oxide composition containing $B_2O_3$ to enrich the $B_2O_3$ present on its surface. This method comprises heating said composition in oxygen or an oxygen-containing environment (e.g., air) at an elevated temperature for a time sufficient to enrich the $B_2O_3$ on the surface of the composition by at least a factor of two compared to the surface $B_2O_3$ content of the untreated bulk composition. Further provided is a method to reduce the amount of $B_2O_3$ present in a bulk chromium oxide composition containing $B_2O_3$ by first treating the bulk chromium oxide composition to enrich $B_2O_3$ present on its surface as indicated above, and contacting the surface-enriched composition with HF in the vapor-phase at an elevated temperature.

Processes are provided herein which comprise contacting 1,1-difluoroethane in the vapor phase with a trivalent chromium catalyst (preferably a trivalent chromium catalyst having primarily the morphology of alpha-chromium oxide and/or containing less than 1000 ppm alkali metal as the alkali metal oxide) wherein chromium is at least 95 atom percent of the metallic cations of said catalyst, at a temperature between about 225° C. and 375° C. Advantageous embodiments of these processes are provided wherein the catalyst is prepared by reducing $B_2O_3$ present in a bulk chromium oxide composition as indicated above. Further advantageous embodiments are provided wherein chromium is at least 99 atom percent of the metallic cations of the catalyst. Also provided are advantageous embodiments wherein the space velocity is from about 200 volumes to 2000 volumes of 1,1-difluoroethane per volume of catalyst per hour.

DETAILED DISCUSSION

The present invention provides a process for the manufacture of vinyl fluoride by contacting 1,1-difluoroethane in the presence of selected high purity trivalent chromium catalysts. Preferred catalysts include $Cr_2O_3$. Particularly preferred is $Cr_2O_3$ having primarily the morphology of alpha-chromium oxide (especially $Cr_2O_3$ consisting essentially of alpha-chromium oxide). Included is $Cr_2O_3$ prepared by pyrolysis of $(NH_4)_2Cr_2O_7$.

The $Cr_2O_3$ catalyst prepared by the pyrolysis of ammonium dichromate suitable for the process of this invention can be prepared by any method known in the art including those disclosed in U.S. Pat. Nos. 4,843,181and 5.036,036, which are hereby incorporated herein by reference. The $Cr_2O_3$ obtained in this manner may contain low levels of contaminants (e.g., potassium) which are present as a result of the manufacturing process for the original $(NH_4)_2Cr_2O_7$. The level of potassium or other water soluble impurities may be reduced by a water-washing in a conventional manner.

Other $Cr_2O_3$ catalysts which may be used in the process of this invention include amorphous chromium oxide catalysts which have been treated to convert them to exhibit alpha-chromium oxide morphology as determined by x-ray diffraction. While several methods for treatment might be available, a useful method is to heat amorphous chromium oxide to an elevated temperature (e.g., between 400 and 500° C.) in air for a sufficient period of time (usually from 24 to 48 hours).

Bulk chromium oxide compositions containing $B_2O_3$ may be heated in oxygen, in air or in other oxygen-containing environments at an elevated temperature (e.g., between 400 and 500° C.) for a time sufficient to enrich the $B_2O_3$ on the surface of the composition. It is generally desirable to enrich the $B_2O_3$ on the surface in this manner by at least a factor of two compared to the surface analysis of the untreated bulk composition. This method may be used, for example, for enriching surface $B_2O_3$ in bulk chromium oxide compositions wherein Cr is from about 95 to 99 atom percent of the metallic cations of the composition and B is from about 0.1 to 5 atom percent of the metallic cations of the composition. When the starting bulk chromium oxide composition is amorphous, this heat treatment can be used to simultaneously provide alpha-chromium oxide morphology within the composition. The amount of $B_2O_3$ present on the surface of the chromium oxide composition may then be reduced by treatment with HF in the vapor phase at an elevated temperature (e.g., from 200 to 400° C.).

For example, Guignet's green (a commercially available green pigment and which has typical compositions as follows: $Cr_2O_3$ 79 to 83%, $H_2O$ 16 to 18%, $B_2O_3$ 1.5 to 2.7%) can be treated by this method of surface enrichment to convert it essentially to the alpha-form. The boron present as $B_2O_3$ can be removed after this heat treatment by treatment of the heat-treated material with HF at an elevated temperature (usually from 200 to 300° C.) to remove the boron as $BF_3$. During this treatment with HF minor amounts of the chromium oxide may be converted to chromium oxyfluorides. Prior to treatment the Guignet's green is considered to have little, if any, alpha-chromium oxide morphology. After the above described heat treatment to remove boron, the resulting chromium catalyst has a x-ray pattern typical of alpha-chromium oxide.

The structure of the catalyst is not critical and may, for example, include pellets, powders or granules. Preferably, the trivalent chromium catalyst contains less than 1000 ppm alkali metal, as the alkali metal oxide, and less than 2000 ppm boron, as $B_2O_3$. It has been found particularly advantageous for converting 1,1-difluoroethane, to employ catalysts wherein the metallic cations of the catalyst are at least about 99 atom percent chromium, more preferably about 99.5 atom percent or more chromium.

Generally, the $Cr_2O_3$ catalyst will be treated with HF before use. It is thought that this converts some of the surface chrome oxide to chromium oxyfluorides. This pretreatment can be accomplished by placing the $Cr_2O_3$ in a suitable container, which can be the reactor to be used to perform the reaction of the instant invention, and thereafter, passing HF over the dried $Cr_2O_3$ so as to partially saturate the $Cr_2O_3$ with HF. This is conveniently carried out by passing HF over the $Cr_2O_3$ for a period of time (e.g., about 15 to 300 minutes) at a temperature of, for example, about 200° C. to about 450° C. Nevertheless, this HF treatment is not essential.

The reaction temperature will normally be within the range from about 200° C. to about 400° C., preferably about 225° C. to 375° C. The 1,1-difluoroethane is passed over the catalyst at a rate of about 200 volumes to about 2000 volumes per volume of catalyst per hour; preferably 400 volumes to 1000 volumes per volume of catalyst per hour.

The reaction pressure can be subatmospheric, atmospheric or superatmospheric. Generally, near atmospheric pressures are preferred.

The dehydrofluorination of 1,1-difluoroethane to vinyl fluoride and hydrogen fluoride is an equilibrium reaction. According to published literature the following equilibrium concentrations of vinyl fluoride (VF) have been determined; about 13% VF at 227° C., about 40% VF at 327° C. and about 99% VF at 427° C.

Unreacted starting material can be recycled to the reactor for the production of additional ($Ch_2$=CHF. Vinyl fluoride (b.p. −72° C.) may be recovered from the reaction product and any unreacted 1,1-difluoroethane (b.p. −25° C.) by conventional procedures such as distillation.

The process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following preferred specific embodiments are to be construed as illustrative, and not as constraining the remainder of the disclosure in any way whatsoever.

EXAMPLES

General Procedure for Catalyst Evaluation

Catalyst evaluation was done in a fixed-bed reactor consisting of a 12" (30.5 cm)×½" (1.3 cm) carbon steel tube maintained in a fluidized sandbath. The temperature was measured at the center of the bed. The feed material were sent upflow through the reactor. The reactor was charged with the catalyst to be evaluated. It was then heated to about 250° C. in a flow of nitrogen (50 cc/min) for about 30 minutes. The temperature was reduced to 175° C. and a HF:Nitrogen flow in the ratio of 1:1 (total flow 100 cc/min) was passed through. After HF was observed in the reactor exit, the HF/Nitrogen ratio was changed to 4:1 (total flow 100 cc/min) and the temperature of the reactor gradually increased to 350–400° C. The reactor contents were kept at 350–400° C. for about 30 minutes. The reactor contents were then brought to the desired operating conditions for catalyst evaluations.

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×⅛" (0.32 cm) diameter tube containing Krytox™ perfluorinated polyether on an inert carbon support. The helium flow was 35 mL/min. Gas chromatographic conditions were 70° C. for an initial hold period of three minutes followed by temperature programming to 180° C. at a rate of 6° C./minute. Unless indicated otherwise, the reported results are in mole %.

The bulk of the reactor effluent containing organic products and also inorganic acid HF was treated with aqueous caustic to neutralize the acid prior to disposal.

Legend 1141 is $CH_2$=CHF

F152a is $CH_3CHF_2$

SV is Space Velocity (volume F152a per volume catalyst per hour)

EXAMPLE 1

Dehydrofluorination of F152a

Catalyst: Guignet's Green $Cr_2O_3$ 5 cc, 3.4 g, 10 to 20 mesh (2.0 to 0.84 mm)

A commercially available Guignet's Green $Cr_2O_3$ was used as the catalyst and was treated with HF to 400° C. prior to use. Results under a variety of conditions are shown in the table.

| Temp. ° C. | F152a cc/min | SV | $C_2H_2$ | $C_2H_4$ | F1141 | F152a |
|---|---|---|---|---|---|---|
| 250 | 25 | 300 | 0.0 | 0.0 | 19.6 | 80.3 |
| 260 | 25 | 300 | 0.0 | 0.0 | 24.5 | 75.5 |
| 280 | 25 | 300 | 0.0 | 0.0 | 35.7 | 64.2 |
| 300 | 25 | 300 | 0.1 | 0.1 | 48.7 | 51.1 |
| 320 | 25 | 300 | 0.3 | 0.1 | 61.6 | 37.9 |
| 340 | 25 | 300 | 0.7 | 0.2 | 72.7 | 26.3 |
| 350 | 25 | 300 | 0.9 | 0.2 | 77.2 | 21.6 |
| 350 | 50 | 600 | 0.4 | 0.1 | 77.8 | 21.7 |

-continued

| Temp. ° C. | F152a cc/min | SV | $C_2H_2$ | $C_2H_4$ | F1141 | F152a |
|---|---|---|---|---|---|---|
| 350 | 75 | 900 | 0.2 | 0.0 | 76.9 | 22.8 |
| 350 | 100 | 1200 | 0.1 | 0.0 | 75.3 | 24.6 |
| 375 | 15 | 200 | 1.8 | 0.2 | 85.1 | 12.6 |

Trace amounts of methane (less than 0.1%) were found in some of the runs.

EXAMPLE 2

Dehydrofluorination of F152a

Catalyst: alpha-$Cr_2O_3$ 5 cc, 7.4 g, 10 to 20 mesh (2.0 to 0.84 mm)

Alpha-chromium oxide obtained from the pyrolysis of ammonium dichromate prepared according to the procedure described in U.S. Pat. No. 5,036,036 was used. The catalyst was treated with HF to 400° C. prior to use. Results under a variety of conditions are shown in the table.

| Temp. ° C. | F152a cc/min | SV | $C_2H_2$ | $C_2H_4$ | F1141 | F152a |
|---|---|---|---|---|---|---|
| 250 | 25 | 300 | 0.0 | 0.0 | 19.3 | 80.6 |
| 280 | 25 | 300 | 0.0 | 0.1 | 35.2 | 64.6 |
| 300 | 25 | 300 | 0.1 | 0.2 | 47.7 | 51.7 |
| 320 | 25 | 300 | 0.5 | 0.4 | 60.5 | 38.2 |
| 340 | 25 | 300 | 1.4 | 0.6 | 70.8 | 26.4 |
| 350 | 25 | 300 | 2.2 | 0.8 | 74.7 | 21.5 |
| 350 | 50 | 600 | 1.9 | 0.1 | 76.5 | 21.1 |
| 350 | 75 | 900 | 1.6 | 0.1 | 76.5 | 21.4 |
| 350 | 100 | 1200 | 1.2 | 0.0 | 76.7 | 21.9 |

Small quantities (up to about 1%) of methane and other unidentified products were present.

EXAMPLE 3

Dehydrofluorination of F152a (Life Test)

Catalyst: Guignet's Green $Cr_2O_3$ 5 cc, 3.4 g, 10 to 20 mesh (2.0 to 0.84 mm)

To the reactor maintained at 275° C. was fed 50 cc/min (SV was 600) of F152a. The contact time was 6 seconds. The commercially available Guignet's Green $Cr_2O_3$ catalyst was treated with HF to 400° C. prior to use. Results under a variety of conditions are shown in the table.

| Hours | F1141 | F152a |
|---|---|---|
| 10 | 31.6 | 68.4 |
| 48 | 30.1 | 70.0 |
| 72 | 28.7 | 71.3 |
| 90 | 27.6 | 72.4 |
| 108 | 26.1 | 74.0 |
| 129 | 24.1 | 76.0 |

EXAMPLE 4

Dehydrofluorination of F152a (Life Test)

Catalyst: alpha-$Cr_2O_3$ 5 cc, 7.4 g, 10 to 20 mesh (2.0 to 0.84 mm)

The alpha-chromium oxide was prepared in the same manner as described in Example 2. To the reactor maintained at 275° C. was fed 50 cc/min (SV was 600) of F152a. The contact time was 6 seconds. The catalyst was treated with HF to 400° C. prior to use. Results under a variety of conditions are shown in the table.

| Hours | F1141 | F152a |
|---|---|---|
| 9 | 31.4 | 68.6 |
| 69 | 31.5 | 68.5 |
| 99 | 31.3 | 68.7 |
| 129 | 30.8 | 69.2 |
| 150 | 30.0 | 70.0 |
| 162 | 29.8 | 70.2 |

Comparison of the data in Example 3 and Example 4 shows the superiority of alpha-chromium oxide in terms of catalyst stability

EXAMPLE 5

Dehydrofluorination of F152a

Catalyst: alpha-chromium oxide 5 cc, 6.5 g, 10 to 20 mesh (2.0 to 0.84 mm)

Alpha-chromium oxide prepared by the precipitation of chromium hydroxide from chromium nitrate followed by calcination in air at 500° C. for 72 hours was used. The catalyst was activated in a stream of HF to 400° C. prior to use. Results under a variety of conditions are shown in the table.

| Temp. ° C. | F152a cc/min | SV | $C_2H_2$ | $C_2H_4$ | F1141 | F152a |
|---|---|---|---|---|---|---|
| 250 | 25 | 300 | 0.0 | 0.0 | 19.9 | 80.0 |
| 260 | 25 | 300 | 0.0 | 0.0 | 24.1 | 75.8 |
| 280 | 25 | 300 | 0.1 | 0.0 | 35.1 | 64.7 |
| 300 | 25 | 300 | 0.3 | 0.0 | 47.9 | 51.7 |
| 320 | 25 | 300 | 0.8 | 0.2 | 60.8 | 38.2 |
| 340 | 25 | 300 | 1.7 | 0.1 | 71.5 | 26.6 |
| 350 | 25 | 300 | 2.4 | 0.2 | 75.5 | 21.6 |
| 350 | 50 | 600 | 2.1 | 0.1 | 76.3 | 21.4 |
| 350 | 75 | 900 | 1.6 | 0.0 | 76.6 | 21.7 |
| 350 | 100 | 1200 | 1.2 | 0.0 | 76.1 | 22.7 |

Small quantities of other unidentified products were present.

EXAMPLE 6

Dehydrofluorination of F152a

Catalyst: Calcined Guignet's Green $Cr_2O_3$ 5 cc, 3.3 g, 10 to 20 mesh (2.0 to 0.84 mm)

A commercially available sample of Guignet's Green $Cr_2O_3$ was calcined in air at 500° C. for 72 hours prior to use. X-ray examination showed that it was converted essentially to alpha-chromium oxide. To the reactor was fed 25 cc/min (SV was 300) of F152a. The catalyst was not activated with HF prior to use. The results reported are in area %. Results under a variety of conditions are shown in the table.

| Time (Hours) | Temp. (° C.) | F1141 | F152a |
|---|---|---|---|
| 1.0 | 250 | 0.4 | 99.6 |
| 2.0 | 260 | 0.9 | 99.1 |
| 3.0 | 280 | 31.3 | 68.7 |
| 4.0 | 280 | 21.1 | 78.9 |
| 5.0 | 280 | 30.3 | 69.7 |
| 6.0 | 280 | 31.5 | 68.5 |
| 8.0 | 290 | 39.1 | 60.9 |
| 9.0 | 300 | 46.1 | 53.9 |
| 9.5 | 310 | 53.5 | 46.5 |
| 10.0 | 320 | 60.5 | 39.5 |
| 10.5 | 330 | 66.9 | 33.0 |
| 11.0 | 340 | 72.9 | 27.0 |
| 12.0 | 350 | 77.3 | 22.6 |

EXAMPLE 7

Dehydrofluorination of F152a

Catalyst: Calcined Guignet's Green $Cr_2O_3$ 5 cc. 3.3 g, 10 to 20 mesh (2.0 to 0.84 mm)

A commercially available sample of Guignet's Green $Cr_2O_3$ was calcined in air at 500° C. for 72 hours and then activated in a stream of HF to 400° C. prior to use. During the course of the activation considerable amounts of boron trifluoride were produced which hydrolyzed to boric acid in water and was identified as boric acid by standard methods. Examination of the catalyst surface via x-ray photoelectron spectroscopy showed that about 10% of the catalyst surface contained boric oxide (expressed as boron) showing an enrichment of boron on the catalyst surface from the bulk of the catalyst during calcination at 500° C. in air (compared to about 3% before calcination) before treatment with HF. After HF treatment, there was no boron detected by the same technique. Results under a variety of conditions are shown in the table.

| Temp. ° C. | F152a cc/min | SV | F1141 | F152a |
|---|---|---|---|---|
| 250 | 25 | 300 | 20.1 | 79.9 |
| 280 | 25 | 300 | 35.8 | 64.2 |
| 300 | 25 | 300 | 49.0 | 51.0 |
| 320 | 25 | 300 | 62.3 | 37.6 |
| 340 | 25 | 300 | 74.0 | 25.7 |
| 350 | 25 | 300 | 78.5 | 21.1 |
| 350 | 50 | 600 | 78.2 | 21.7 |
| 350 | 75 | 900 | 75.7 | 24.3 |
| 350 | 100 | 1200 | 71.6 | 28.2 |

There were small quantities of unidentified products at higher temperatures.

EXAMPLE 8

Dehydrofluorination of F152a

Catalyst: alpha-chromium oxide 10 cc, 14.4 g, 10 to 20 mesh (2.0 to 0.84 mm)

Alpha-chromium oxide obtained from the pyrolysis of ammonium dichromate prepared according to the procedure described in U.S. Pat. No. 5,036,036 was used. It was activated in a stream of HF up to 350° C. prior to use. The results reported are in area %. Results under a variety of conditions are shown in the table.

| Time Hours | Temp. ° C. | F152a cc/min | SV | F1141 | F152a |
|---|---|---|---|---|---|
| 15.0 | 200 | 50 | 300 | 6.0 | 94.0 |
| 16.0 | 200 | 100 | 600 | 6.0 | 94.0 |
| 22.0 | 225 | 100 | 600 | 10.8 | 89.2 |
| 38.0 | 245 | 100 | 600 | 17.3 | 82.7 |
| 41.0 | 245 | 150 | 900 | 17.4 | 82.6 |
| 44.0 | 245 | 200 | 1200 | 17.3 | 82.7 |
| 46.0 | 245 | 300 | 1800 | 16.7 | 83.3 |
| 47.5 | 245 | 400 | 2400 | 16.0 | 84.0 |

EXAMPLE 9

Dehydrofluorination of F152a

Catalyst: High surface area amorphous chromium oxide 5 cc, 6.5 g, 10 to 20 mesh (2.0 to 0.84 mm)

A commercial sample of chromium oxide having a surface area of about 200 $m^2/g$ was used. X-ray diffraction pattern of this sample showed that it was essentially amorphous. The catalyst was activated in a stream of HF up to 350° C. prior to use. Results under a variety of conditions are shown in the table.

| Time Hours | Temp. ° C. | F152a cc/min | SV | F1141 | F152a |
|---|---|---|---|---|---|
| 5 | 245 | 50 | 600 | 15.1 | 84.9 |
| 19 | 245 | 50 | 600 | 15.5 | 84.5 |
| 22 | 245 | 100 | 1200 | 13.2 | 86.6 |
| 24 | 275 | 100 | 1200 | 23.8 | 76.2 |
| 40 | 275 | 100 | 1200 | 21.6 | 78.4 |
| 49 | 275 | 100 | 1200 | 21.0 | 79.0 |

Comparison of results obtained in Example 9 with those in Example 8 at comparable contact time shows that the conversion obtained using alpha-chromium oxide is higher and the stability of the alpha-chromium oxide catalyst is superior.

What is claimed is:

1. A process for the production of vinyl fluoride comprising:

contacting 1,1-difluroethane in the vapor phase with a trivalent chromium catalyst having primarily the morphology of alpha-chromium oxide and containing less than 1000 ppm alkali metal as the alkali metal oxide, wherein chromium is at least 99 atom percent of the metallic cations of said catalyst, at a temperature between about 225° C. and 375° C.

2. The process of claim 1 wherein the space velocity is from about 200 volumes to 2000 volumes of 1,1-difluoroethane per volume of catalyst per hour.

* * * * *

UNITED STATES PATENT AND TRADEMARK OFFICE
CERTIFICATE OF CORRECTION

PATENT NO. : 6,359,183 B1 Page 1 of 1
DATED : March 19, 2002
INVENTOR(S) : George W. Coulston et al.

It is certified that error appears in the above-identified patent and that said Letters Patent is hereby corrected as shown below:

<u>Title page,</u>
Item [12], delete "Christoph et al." and insert in its place -- Coulston et al. --.
Item [75], delete "Frank J. Christoph, Elkton, MD (US);".

Signed and Sealed this

Fifth Day of August, 2003

JAMES E. ROGAN
*Director of the United States Patent and Trademark Office*